United States Patent [19]

Peters et al.

[11] Patent Number: 5,320,959
[45] Date of Patent: Jun. 14, 1994

[54] LIQUID LIPASE FROM ANIMAL ORIGIN AND METHOD OF PREPARATION

[75] Inventors: James R. Peters, Belleville, Wis.; Jayarama K. Shetty, Elkhart; Donald B. Smith, South Bend, both of Ind.

[73] Assignee: Rhone-Poulenc Inc., Princeton, N.J.

[21] Appl. No.: 567,630

[22] Filed: Aug. 15, 1990

[51] Int. Cl.$^5$ ............................ C12N 9/20; C12P 7/64
[52] U.S. Cl. .................................... 435/198; 435/134
[58] Field of Search ............... 435/198, 226, 134

[56] References Cited

U.S. PATENT DOCUMENTS

| 2,531,329 | 11/1950 | Farnham | 435/226 |
|---|---|---|---|
| 4,065,580 | 12/1977 | Feldman et al. | 435/198 |
| 4,636,468 | 1/1987 | Arbige et al. | 435/198 |
| 4,707,364 | 11/1987 | Barach et al. | 435/198 |
| 4,752,483 | 6/1988 | Hagberg et al. | 426/35 |
| 4,943,530 | 7/1990 | Christner et al. | 435/198 |

OTHER PUBLICATIONS

Kirk-Othmer, "Encyclopedia of Chemical Technology", p. 190 (1980).

*Primary Examiner*—David M. Naff
*Assistant Examiner*—Michael Meller
*Attorney, Agent, or Firm*—John A. Shedden

[57] ABSTRACT

Disclosed is a method for the extraction of lipase from mammalian tissue with which it is associated which involves contacting the tissue with an alkaline, aqueous medium having a pH of from greater than 7.0 up to a level at which the alkalinity will deactivate the lipase.

8 Claims, No Drawings

LIQUID LIPASE FROM ANIMAL ORIGIN AND METHOD OF PREPARATION

BACKGROUND OF THE INVENTION

The commercial application of lipases (esterases) from animal origin are varied. For example, these enzymes find utility in natural flavor production such as in enzymatic modification of lipid food ingredients and in cheese ripening processes by shortening the cheese aging time. The lipases are also useful for the formation of enzyme modified cheese flavor in the production of certain Italian type cheeses such as provolone. They also find utility in butter fat modification, for developing products which are useful in bakery/cereal products, imitation dairy products, margarines, salad dressings and pizza sauces.

The development of flavor in cheese under storage conditions is attributed to a combination of breakdown of products from milk constituents, mostly from fat. The presence of free butyric acid, caproic acid and capric acids in aged cheese is largely due to the action of lipases on cheese fat. Thus, the cheese-ripening time and the flavor profile can be altered by the amount of available lipase in the cheese. Lipases have been extensively used in the production of enzyme modified cheese (EMC). Lipolysed milk fat flavored dairy products are produced by incubation of a pregastric lipase with butter fat or vegetable oils. The resulting hydrolysate is then used as a flavor booster in food products.

Animal lipases have been historically used to enhance the flavor in non-dairy products. The increasing demand for animal lipases in food and dairy industries necessitates the development of an improved processing technology for obtaining higher yields from the limited supply of animal sources.

Animal lipases are typically obtained by drying and grinding calf, kid or lamb gullets to provide a solid, enzyme containing product in which the enzyme is closely associated with the gullet tissue. When used, such as in the making of enzyme modified cheese, the ground gullet bearing the enzyme is added to the vat and blended into the cheese milk. This method suffers from the disadvantage of providing pockets of lipase activity due to the incomplete mixing of the solid lipase containing gullet tissue and the liquid cheese milk. In U.S. Pat. No. 2,531,329 there is disclosed a method for extracting lipase from animal tissue (gullet) using an aqueous solution containing 10% propylene glycol together with sodium chloride at an acidic pH (pH 6.2–6.5).

The advantages of a liquid form of animal lipase are apparent, and it is an object of the present invention to provide such lipase in the liquid form as well as a method for its preparation. A further object is to provide such a method which provides for the extraction of lipase using an alkaline, aqueous medium which does not require additives to enhance extractions by the aqueous medium.

SUMMARY OF THE INVENTION

The present invention is a method of extracting lipase from the tissues of mammals with which it is associated which method comprises contacting the tissue with an aqueous alkaline media having a pH of from greater than 7.0 up to the pH level at which the lipase is inactivated for a time sufficient to cause the dissociation of the lipase from the animal tissue and provide an aqueous solution containing the lipase activity. The aqueous solution is then separated from the remaining animal tissue by solid/liquid separatory techniques. Also included within the scope of the present invention is the aqueous solution of animal lipase.

DESCRIPTION OF THE INVENTION

Conventional sources of animal lipases include the gullets from calf, kid or lamb, although any milk weaned mammal can be regarded as a suitable source. The lipase from these sources is known as pregastric lipase. All mammals, including man, produce these lipases due to the need to break down complex dietary lipids. These lipases remain firmly bound to the gullet tissue when placed in acidic or neutral solutions in the absence of salt and other extractants such as ethylene glycol or propyleneglycol, however, it has now been discovered that lipase can be isolated by extraction using an aqueous alkaline medium. A medium with a pH even nominally above 7.0 is satisfactory for the extraction although a pH of at least 8.0–8.5 is preferred to achieve an extract having maximum stability. Care must be taken to avoid too high a pH since undue alkalinity will inactivate the lipase. The maximum pH at which the extraction can be carried out will vary depending on the animal tissue which is being worked with. Thus, in the case of kid or lamb lipase, the extraction should be carried out at a pH of no more than 8.5 whereas in the case of calf tissue, a maximum pH of up to 11.0 can be employed without causing the enzyme's inactivation. The maximum pH which can be used to extract lipase from other mammals such as rabbits, monkeys or pigs will vary but can be readily determined without undue experimentation.

The extraction is typically carried out using finely ground, wet or dried gullet tissue which is added to the alkaline extraction media, usually with stirring, at a temperature preferably within the range of from 5 to 30° C. The extraction time will vary depending on the particular conditions of extraction, but will typically range from ½ hour to 10 hours. After the extraction is complete, the animal tissue is separated from the lipase solution by liquid/solid separatory techniques such as filtration or centrifugation with decantation to provide a clear enzyme solution. This solution can either be used as is, or it can be further modified such as by drying to produce a powdered product before being added to a system in which the lipase activity is required. A particularly desirable lipase formulation will contain from 20 to 100 lipase forestomach units per gram (LFU/g). The lipase activity is determined by measuring the free butyric acid liberated from tribytryin substrate using a pH-stat under standard conditions, i.e. pH 6.2, 42° C. as described in FCC 111/General Tests and Apparatus/493. One LFU is the activity that releases 1.25 $\mu$mol of butyric acid per minute under the conditions of the assay. Activity of the enzyme preparation is calculated by the following formula:

$$LFU/g = \frac{R \times 0.025 \times 10^3}{W \times 1.25}$$

where W is the weight, in grams, of the enzyme preparation contained in the 1.0 ml of sample preparation taken for analysis, R is titrant delivery rate in ml/min., and 0.025 is the normality of the titrant.

The above described assay technique was used in the following examples which further illustrate the method of practicing the present invention and the results achieved thereby.

EXAMPLE 1: SEPARATION OF TISSUE-BOUND LIPASE FROM GULLET OF LAMB, CALF AND KID

Frozen gullets of calf, lamb and kid were thawed and ground in a meat grinder. One hundred grams of ground lamb gullet was suspended in 1.0 liter of distilled water and the suspension homogenized for five minutes using a mechanical homogenizer. Aliquots (100 ml) were placed in individual beakers and the pH was adjusted to pH 5.0, 6.0, 6.5, 7.0, 7.5, 8.0, 8.5 and 9.0 respectively. Samples were placed in an ice bath and stirred for 60 minutes.

A portion of the suspension was then centrifuged to separate the insolubles (tissue), and the clear supernatant was tested for enzyme activity. Lipase activity was determined for corresponding supernatant and non-centrifuged samples by autotitration methods. The percentage activity appearing in the supernatant was calculated at each pH value.

The experiment was repeated under identical conditions using ground gullet of kid and calf (except that the pH was raised incrementally to 12.0 in the case of the calf tissue). The effect of pH on the extraction of lipase from the gullets is presented in Tables 1a, b and c.

TABLE 1 pH EFFECT ON EXTRACTION OF LIPASE

A. LAMB

| Sample Assayed | Non-Centrifuged LFU/ml | Supernatant LFU/ml | Activity Sup/Meat |
|---|---|---|---|
| pH 5.0 | 9.6 | 0.6 | 6.3% |
| pH 5.0 | 12.0 | 3.8 | 31.7% |
| pH 6.0 | 12.8 | 3.8 | 29.7% |
| pH 6.5 | 13.8 | 7.6 | 55.1% |
| pH 7.0 | 16.8 | 8.2 | 48.8% |
| pH 7.5 | 13.6 | 13.0 | 95.6% |
| pH 8.0 | 18.2 | 18.2 | 100.0% |
| pH 8.5 | 17.4 | 17.4 | 100.0% |
| pH 9.0 | 5.8 | 4.0 | 69.0% |

B. CALF

| Sample Assayed | Non-Centrifuged LFU/ml | Supernatant LFU/ml | Activity Sup/Meat |
|---|---|---|---|
| pH 5.0 | 24.0 | 1.0 | 4.2% |
| pH 5.5 | 24.4 | 2.8 | 11.5% |
| pH 6.0 | 27.1 | 5.6 | 20.7% |
| pH 6.5 | 30.6 | 4.8 | 15.7% |
| pH 7.0 | 25.3 | 5.3 | 20.9% |
| pH 7.5 | 26.0 | 17.6 | 29.2% |
| pH 8.0 | 27.6 | 10.6 | 138.4% |
| pH 8.5 | 42.4 | 23.8 | 156.1% |
| pH 9.0 | 48.2 | 32.4 | 67.2% |
| pH 9.5 | 44.4 | 37.7 | 84.9% |
| pH 10.0 | 46.6 | 43.2 | 92.7% |
| pH 10.5 | 46.8 | 47.0 | 100.4% |
| pH 11.0 | 35.2 | 34.0 | 96.5% |
| pH 11.5 | 26.0 | 28.6 | 110.0% |
| pH 12.0 | 8.7 | 9.0 | 103.0% |

C. KID

| Sample Assayed | Non-Centrifuged LFU/ml | Supernatant LFU/ml | Activity Bind Index* |
|---|---|---|---|
| pH 5.0 | 83.2 | 14.9 | 17.9% |
| pH 5.5 | 102.2 | 60.5 | 59.2% |
| pH 6.0 | 97.0 | 100.0 | 103.1% |
| pH 6.5 | 180.4 | 113.2 | 62.7% |
| pH 7.0 | 173.5 | 122.0 | 70.3% |
| pH 7.5 | 189.0 | 178.5 | 94.4% |
| pH 8.0 | 223.0 | 204.0 | 91.5% |
| pH 8.5 | 275.4 | 289.2 | 105.0% |

TABLE 1-continued pH EFFECT ON EXTRACTION OF LIPASE

| pH 9.0 | 140.4 | 148.0 | 105.4% |

*Binding Index = % lipase solubilized

From the above data it can be determined that the separation of lipase from ground gullet is increased with increasing pH and reaches a maximum around pH 8.0–8.5. A pH greater than 8.5 caused the inactivation of the enzyme in the case of its extraction from lamb and kid tissue whereas lipase from calf tissue was not inactivated until a pH of greater than 10 was reached. More than 50% of the lipase was associated with the tissue at pH 6.0 and binding of lipase with tissue was increased with decreasing pH. It is assumed that the increase in the negative charge of the lipase in the alkaline pH may have caused either the dissociation of aggregated lipase molecules or separation of tissue-bound lipase. In any case, alkaline pH treatment of ground gullet separated the tissue-bound lipase, resulting in a marked increase in the recovery of the enzyme.

EXAMPLE 2: EFFECT OF pH ON THE EXTRACTION OF LIPASE FROM COMMERCIAL LIPASE POWDER PRODUCT

Commercially available lipase product is basically a dry gullet powder. The effect of pH on the extraction of lipase from this powder product was studied. A 2.5% (2.5 g/100 ml) suspension of the powder in water was made and the pH of the suspension adjusted to various pHs using alkali (0.2 N). The suspension was then stirred at 5° C. for one hour. The solubilized lipase was separated by centrifugation. The effect of pH on the lipase extraction from lipase product was determined by measuring the lipase activity before and after centrifugation. The data presented in Table 2 clearly demonstrate a dramatic effect of pH on the dissociation of tissue bound lipase.

TABLE 2

EFFECT OF pH ON THE EXTRACTION OF LIPASE FROM POWDERED LIPASE PRODUCT

| EXTRACTION pH | NON-FILTERED LFU/ml | FILTERED LFU/ml |
|---|---|---|
| A. KID POWDER | | |
| pH 5.0 | 12.5 | 6.0 |
| pH 5.5 | 15.6 | 10.4 |
| pH 6.0 | 19.6 | 12.4 |
| pH 6.5 | 24.0 | 17.2 |
| pH 7.0 | 25.6 | 21.7 |
| pH 7.5 | 24.8 | 23.6 |
| pH 8.0 | 24.4 | 24.4 |
| pH 8.5 | 24.4 | 24.8 |
| pH 9.0 | 23.8 | 18.8 |
| B. CALF POWDER | | |
| pH 5.0 | 6.2 | 0.1 |
| pH 5.5 | 7.5 | 0.6 |
| pH 6.0 | 8.7 | 1.0 |
| pH 6.5 | 7.5 | 1.6 |
| pH 7.0 | 8.0 | 2.9 |
| pH 7.5 | 9.0 | 3.9 |
| pH 8.0 | 8.4 | 4.2 |
| pH 8.5 | 6.8 | 4.5 |
| pH 9.0 | 7.2 | 5.1 |
| C. LAMB POWDER | | |
| pH 5.0 | 3.3 | 0.5 |
| pH 5.5 | 3.6 | 0.6 |
| pH 6.0 | 3.0 | 0.7 |
| pH 6.5 | 3.9 | 2.6 |
| pH 7.0 | 3.7 | 3.3 |
| pH 7.5 | 4.5 | 4.0 |
| pH 8.0 | 5.0 | 4.5 |

TABLE 2-continued

EFFECT OF pH ON THE EXTRACTION OF LIPASE FROM POWDERED LIPASE PRODUCT

| EXTRACTION pH | NON-FILTERED LFU/ml | FILTERED LFU/ml |
|---|---|---|
| pH 8.5 | 5.6 | 4.1 |
| pH 9.0 | 4.8 | 3.3 |

EXAMPLE 3:

The binding of lipase to the ground tissue was determined at two different pHs (pH 6.0 and 8.5/10.5 for calf) as described in Example 1. After alkaline extraction of the enzyme, the pH of the treated materials was decreased to pH 6.0. The suspension was stirred for another 30 minutes at 5° C. The lipase activity was determined for corresponding supernatant and non-centrifuged samples. The results of this experiment are summarized in Table 3.

TABLE 3

Effect of pH on the Extraction of Lipase from Ground Gullets

LAMB

| pH 6.0 | pH 8.5 | pH 6.0 |
|---|---|---|
| Non-filtered (15.2 LFU/ml) | Non-filtered (33.3 LFU/ml) | Non-filtered (29.8 LFU/ml) |
| Filtrate (2.6 LFU/ml) | Filtrate (29.2 LFU/ml) | Filtrate (14.6 LFU/ml) |
| % Adsorbed (83) | % Adsorbed (12) | % Adsorbed (51) |

CALF

| pH 6.0 | pH 10.5 | pH 6.0 |
|---|---|---|
| Non-filtered (10.9 LFU/ml) | Non-filtered (15.6 LFU/ml) | Non-filtered (15.1 LFU/ml) |
| Filtrate (1.2 LFU/ml) | Filtrate (16.4 LFU/ml) | Filtrate (1.3 LFU/ml) |
| % Adsorbed (89) | % Adsorbed (0) | % Adsorbed (91.4) |

KID

| pH 6.0 | pH 8.5 | pH 6.0 |
|---|---|---|
| Non-filtered | Non-filtered | Non-filtered |

TABLE 3-continued

Effect of pH on the Extraction of Lipase from Ground Gullets

| (93.6 LFU/ml) Filtrate (93.2 LFU/ml) % Adsorbed (0) | (221.0 LFU/ml) Filtrate (221.0 LFU/ml) % Adsorbed (0) | (172.0 LFU/ml) Filtrate (82.8 LFU/ml) % Adsorbed (52) |
|---|---|---|

The data in Table 3 demonstrate the reversible associated of lipase to tissue. In fact, the effect is more profound with calf compared to lamb and kid. Thus, by carrying out the extraction at a pH where reassociation of the enzyme and tissue do not occur, one can realize an increase in the yield of usable enzyme.

What is claimed is:

1. A method for extracting lipase from gullet tissues of mammals with which it is associated which comprises contacting the tissue with an alkaline aqueous media having a pH greater than 7.0 and lower than the pH at which the enzyme is deactivated for a time sufficient to separate the lipase from the animal tissue.

2. The method of claim 1 wherein lipase is extracted from the tissue of a calf, kid or lamb.

3. The method of claim 2 wherein the tissue is from a kid or lamb and the extraction is carried out at a pH no greater than 8.5.

4. The method of claim 3 wherein the pH is from 8.0 to 8.5.

5. The method of claim 2 wherein the tissue is from a calf and the extraction is carried out at a pH no greater than 11.0.

6. The method of claim 5 wherein the pH is from 8.0 to 11.0.

7. The method of claim 1 wherein the extraction is carried out at a temperature within the range of from 5° to 30° C. for a period of time from ½ hour to 10 hours.

8. A method of extracting pregastric lipase from the gullet tissue of a calf, kid or lamb which comprises contacting the tissue with an alkaline aqueous media having a pH of at least 8.0 and, in the case of kid or lamb is no greater than 8.5 and in the case of calf is no greater than 11.0 for a time sufficient to separate the lipase from the tissue.

* * * * *